(12) United States Patent
Chang

(10) Patent No.: US 9,113,780 B2
(45) Date of Patent: Aug. 25, 2015

(54) DEVICE AND METHOD FOR DETECTING OCCURRENCE OF WHEEZE

(75) Inventor: Gwo-Ching Chang, Kaohsiung (TW)

(73) Assignee: I SHOU UNIVERSITY, Kaohsiung (TW)

( * ) Notice: Subject to any disclaimer, the term of this patent is extended or adjusted under 35 U.S.C. 154(b) by 729 days.

(21) Appl. No.: 13/433,729

(22) Filed: Mar. 29, 2012

(65) Prior Publication Data
US 2013/0259240 A1    Oct. 3, 2013

(51) Int. Cl.
*H04R 29/00* (2006.01)
*A61B 7/00* (2006.01)
*H04R 3/00* (2006.01)

(52) U.S. Cl.
CPC . *A61B 7/003* (2013.01); *H04R 3/00* (2013.01); *H04R 2430/03* (2013.01)

(58) Field of Classification Search
CPC .... H04R 29/00; H04R 29/004; H04R 29/005; H04R 29/006; A61B 5/00; A61B 5/002; A61B 5/0022; A61B 5/0024; A61B 5/0028; A61B 5/0051; A61B 5/0082; A61B 5/0093; A61B 5/0097; A61B 5/038; A61B 5/087; A61B 5/091; A61B 5/4803
USPC .......... 381/56, 28, 60, 66, 91, 92, 94.1, 94.2, 381/94.3, 120, 122, 67; 600/529, 528, 533, 600/534, 543, 301, 586, 27; 128/204.23; 700/94
See application file for complete search history.

(56) References Cited

U.S. PATENT DOCUMENTS 6,168,568 B1 *  1/2001  Gavriely ....................... 600/529

OTHER PUBLICATIONS

Kandaswamy et al, "Neural Classification of Lung Sounds Using Wavelet Coefficients", Computers in Biology and Medicine 34, year 2004, p. 523-537.*

* cited by examiner

*Primary Examiner* — Leshui Zhang
(74) *Attorney, Agent, or Firm* — Nixon & Vanderhye P.C.

(57) ABSTRACT

A device for detecting occurrence of wheeze in a lung sound includes an acoustic processing unit, a filtering unit, and an identifying unit. The acoustic processing unit is for obtaining a lung sound and for generating a raw sound signal accordingly. The filtering unit is for filtering the raw sound signal to obtain a filtered signal. The filtered signal has a plurality of sections with respect to the time domain. The identifying unit is for computing an energy value of each of the sections of the filtered signal, and for determining that a wheeze occurs when the energy values of a part of the sections are larger than a predetermined value and duration of the part of the sections is longer than a predetermined observation time.

15 Claims, 6 Drawing Sheets

DEVICE AND METHOD FOR DETECTING OCCURRENCE OF WHEEZE

BACKGROUND OF THE INVENTION

1. Field of the Invention

The invention relates to a device for detecting occurrence of wheeze, more particularly to a device for detecting occurrence of wheeze using biorthogonal wavelet filter banks.

2. Description of the Related Art

Conventionally, irregularity in a lung sound of a patient, such as a wheeze, can be detected using a stethoscope. Nonetheless, a doctor may not accurately detect all occurrences of wheeze using a stethoscope and the judgment made by the doctor on the occurrence of wheeze may be not objective. Additionally, such auscultation method for detecting wheeze cannot provide real time detection for those people who are prone to wheeze.

One way to address the aforementioned drawbacks is to provide a wheeze detecting device for continuously monitoring a lung sound of a patient and for detecting wheeze occurrence in the lung sound. The wheeze detecting device may be practical since the wheeze in the lung sound has a specific property, that is, the wheeze has a dominant frequency of about 400 Hertz or more and a duration of at least 0.25 second.

Generally, an algorithm named Short Time Fourier Transform (STFT) is used for processing and analyzing a sound signal. This algorithm however, involves a fixed window function that may result in difficulty in distinguishing a high-frequency signal and a low-frequency signal from the sound signal. Thus, the STFT algorithm may be unsuitable for analyzing the sound signal of wheeze.

SUMMARY OF THE INVENTION

Therefore, the object of the present invention is to provide a device for accurately and continuously detecting occurrence of wheeze in a lung sound.

Accordingly, a device for detecting occurrence of wheeze in a lung sound of the present invention comprises an acoustic processing unit, a filtering unit, and an identifying unit.

The acoustic processing unit is for obtaining a lung sound and for generating a raw sound signal in time domain accordingly.

The filtering unit is for filtering the raw sound signal to obtain a filtered signal within a specific frequency bandwidth. The filtered signal has a plurality of sections with respect to the time domain.

The identifying unit is for computing an energy value of each of the sections of the filtered signal. The identifying unit is further for determining that a wheeze occurs in the lung sound when the energy values of a part of the sections are larger than a predetermined value and duration of the part of the sections is longer than a predetermined observation time in the time domain.

BRIEF DESCRIPTION OF THE DRAWINGS

Other features and advantages of the present invention will become apparent in the following detailed description of the preferred embodiment with reference to the accompanying drawings, of which.

DETAILED DESCRIPTION OF THE PREFERRED EMBODIMENT

Figure 1:
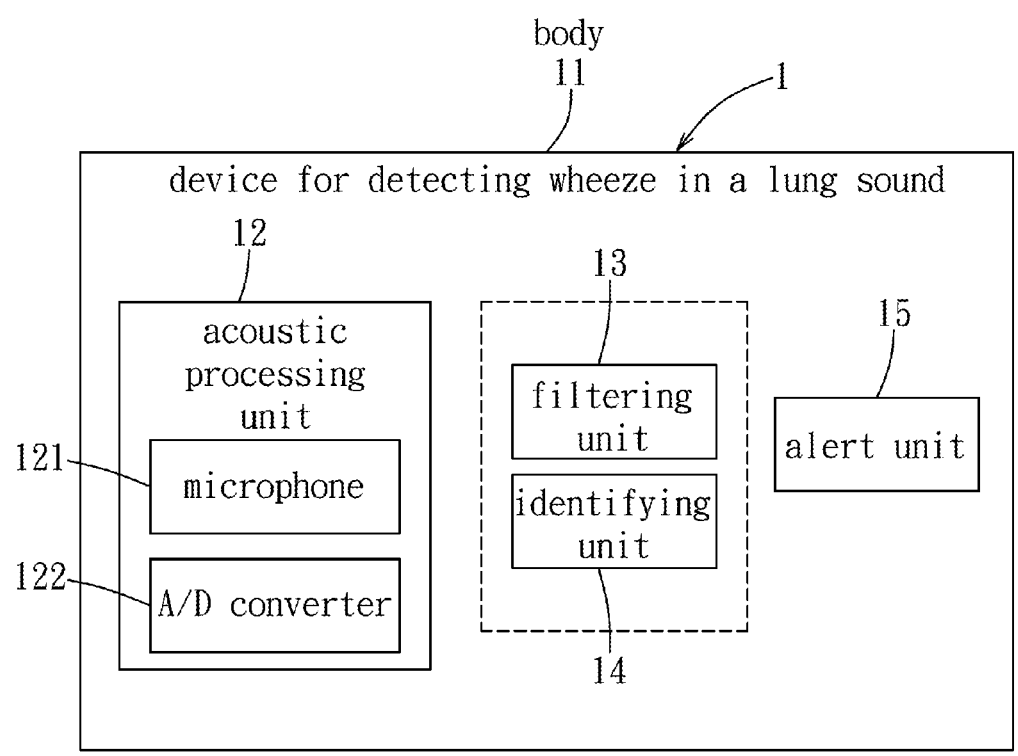
FIG. 1 is a schematic block diagram of a preferred embodiment of a device for detecting occurrence of wheeze in a lung sound according to the invention.

As shown in FIG. 1, the preferred embodiment of a device 1 according to the present invention is for detecting occurrence of wheeze in a lung sound. The device 1 includes an acoustic processing unit 12, a filtering unit 13, an identifying unit 14 and an alert unit 15. The device 1 also includes a body 11 receiving the acoustic processing unit 12, the filtering unit 13 and the identifying unit 14, and the alert unit 15.

In this embodiment, the acoustic processing unit 12 includes a microphone 121 and an analog to digital (A/D) converter 122. The filtering unit 13 includes a plurality of biorthogonal wavelet filter banks. The filtering unit 13 and the identifying unit 14 are implemented using hardware, for example, a logic circuit integrated with a chip capable of detection of wheeze. The device 1 of this embodiment is a portable device that can be attached to a patient for continuously monitoring the patient.

Figure 2:
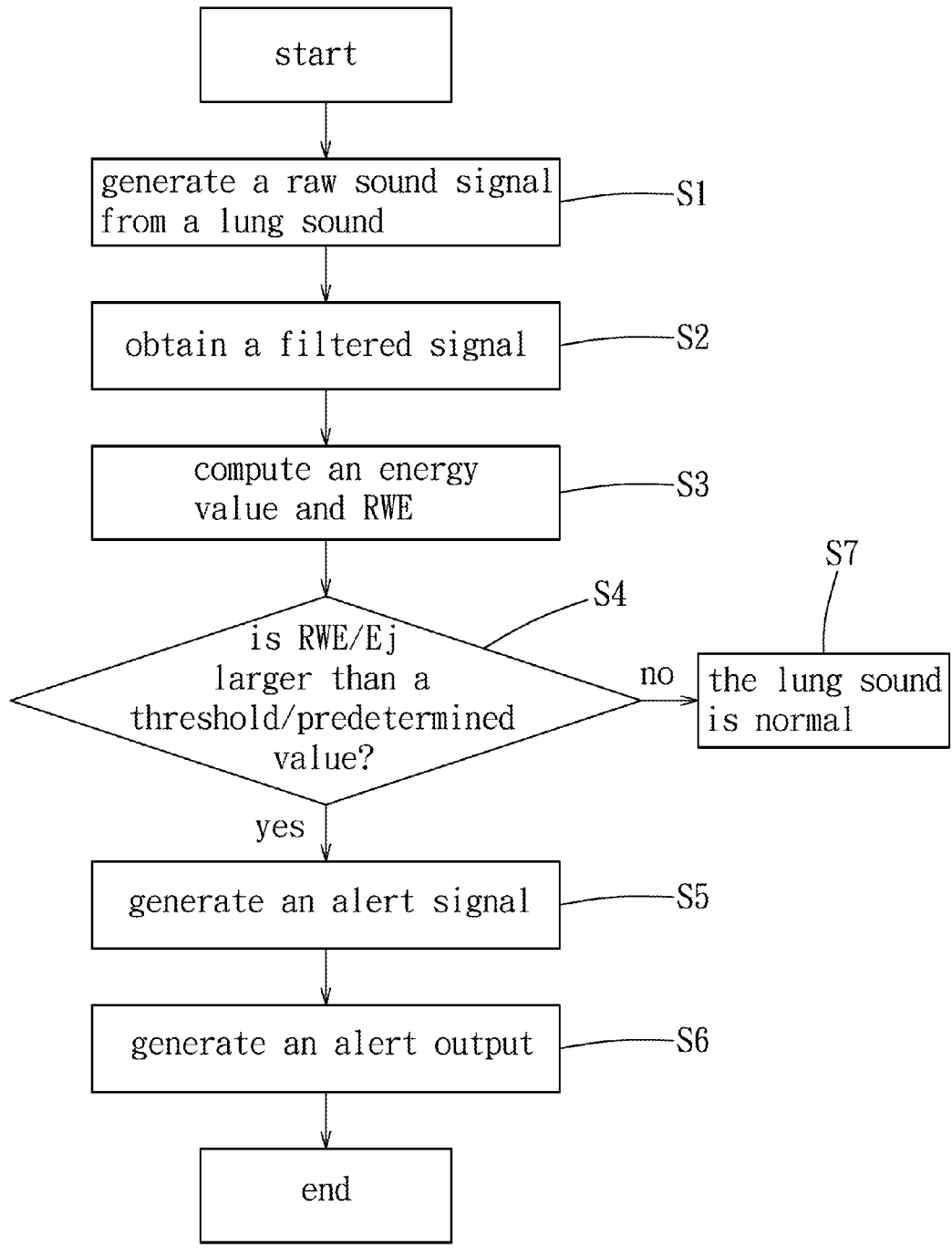
FIG. 2 is a flowchart illustrating steps of a method for detecting occurrence of wheeze in a lung sound.

Steps of a method for detecting occurrence of wheeze are implemented by the device 1 of this embodiment and are described hereinafter with reference to FIG. 2.

In step S1, the microphone 121 of the acoustic processing unit 12 is operable to obtain a lung sound, and the A/D converter 122 of the acoustic processing unit 12 is operable, according to the lung sound thus obtained, to generate a digital raw sound signal in time domain. In this embodiment, the raw sound signal is sampled at 8000 Hertz.

Figure 6:
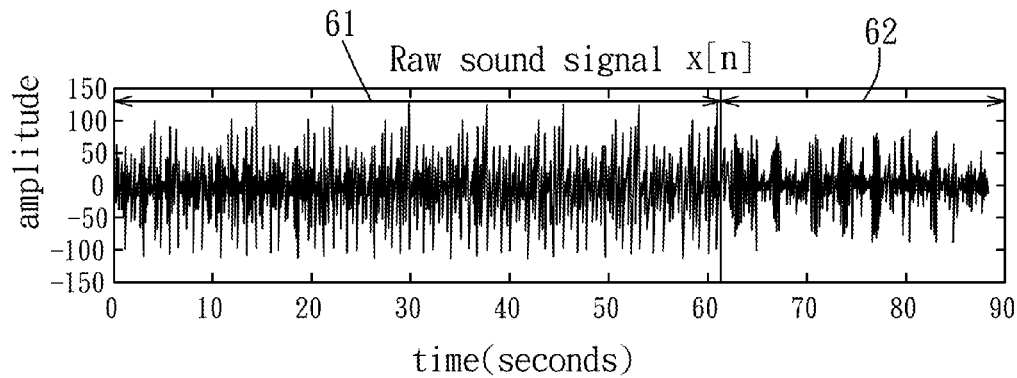
FIG. 6 is a plot illustrating waveform of a raw sound signal associated with a lung sound.

For example, FIG. 6 illustrates a waveform of the raw sound signal including a first portion 61 and a second portion 62. That is, compared with the first portion 61, the second portion 62 of the raw sound signal has a relatively greater frequency at certain time points.

In step S2, the filtering unit 13 of the device 1 is operable to filter the raw sound signal to obtain a filtered signal within a specific frequency bandwidth. In this embodiment, the specific frequency bandwidth of the filtered signal obtained by the filtering unit 13 ranges from 250 Hertz to 500 Hertz, and has a plurality of sections with respect to the time domain. In this embodiment, each of the sections includes 512 sample points.

In this embodiment, each of the biorthogonal wavelet filter banks is a Cohen-Daubechies-Feauveru (CDF) 9/7 tap biorthogonal wavelet filter bank, and has a polyphase structure. Furthermore, the filtering unit 13 is configured to use distributed arithmetic for obtaining the filtered signal. Such configuration of the filtering unit 13 has the advantage of computational efficiency.

Details of the filtering unit 13 of the biorthogonal wavelet filter banks and the corresponding realization are described thereinafter.

Biorthogonal wavelet filter bank is configured to implement a type of a discrete wavelet transform (DWT), and includes high pass and low pass filters. Generally, an output signal produced by passing an input signal through a biorthogonal wavelet filter bank can be expressed as:

$$d[k] = \sum_{n=0}^{N-1} x[n]h[2k-n]; \quad (1)$$

and $$a[k] = \sum_{n=0}^{N-1} x[n]g[2k-n]; \quad (2)$$

where x[n] represents the input signal (i.e., the raw sound signal, generated from the lung sound of the patient, in this embodiment), h[2k–n] represents coefficients of the high pass filter, d[k] represents a high frequency output signal of the high pass filter, g[2k–n] represents coefficients of the low pass filter, and a[k] represents a low frequency output signal of the low pass filter.

Figure 3:
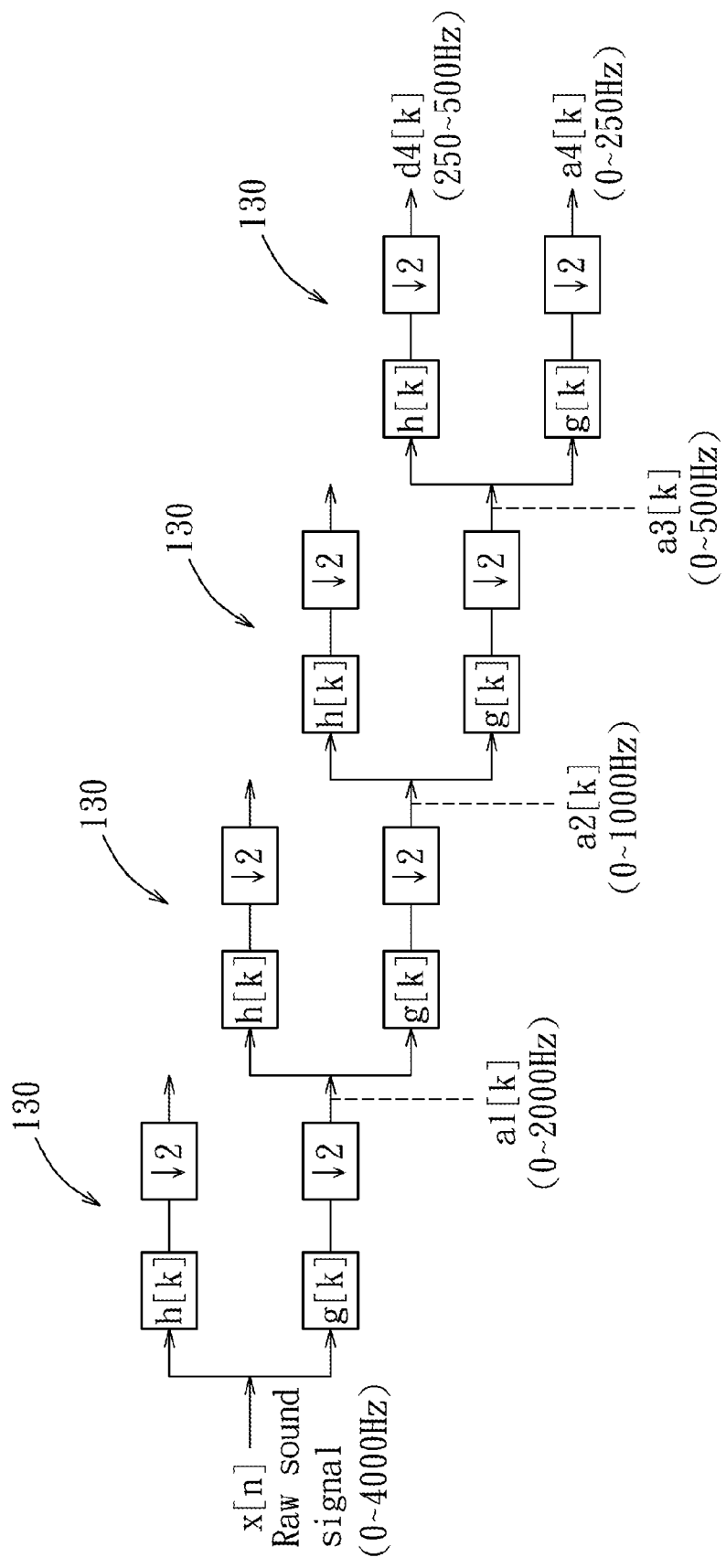
FIG. 3 is a schematic diagram illustrating a four-layer structure of biorthogonal wavelet filter banks.

In this embodiment, the filtering unit 13 is configured as a four-layer structure including four biorthogonal wavelet filter banks 130 arranges in series (see FIG. 3) so as to obtain the filtered signal d4[k] (i.e., the output signal of a fourth one of the biorthogonal wavelet filter banks 130) by passing the raw sound signal x[n] sequentially through the four biorthogonal wavelet filter banks 130. The raw sound signal serves as the input signal of a first one of the biorthogonal wavelet filter banks 130 of the filtering unit 13. Specifically, since the output signal d4[k] covers the specific frequency bandwidth ranging from 250 Hertz to 500 Hertz and corresponding to a frequency of wheeze, it is taken as the filtered signal used for detecting the occurrence of the wheeze.

Figure 4:
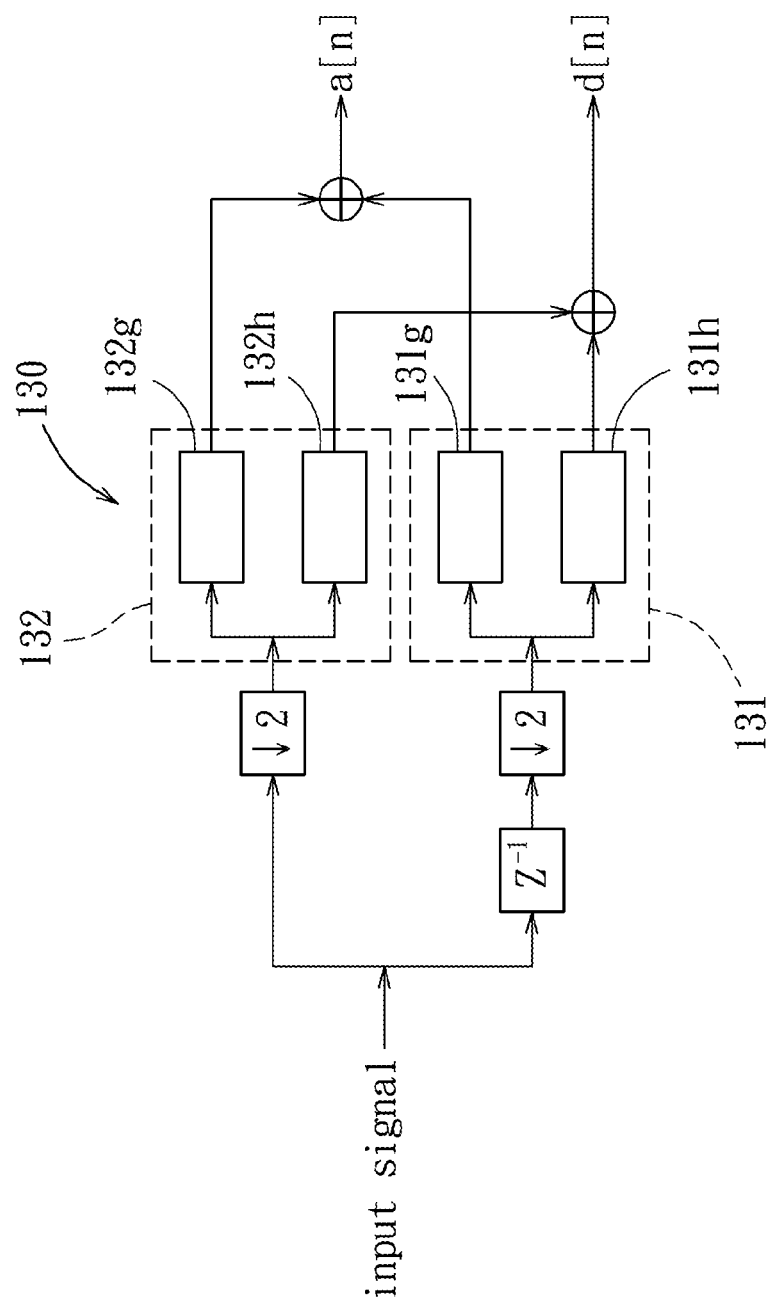
FIG. 4 is a schematic diagram illustrating the biorthogonal wavelet filter bank with a polyphase structure.

Moreover, in the polyphase structure, each of the biorthogonal wavelet filter banks 130 receives an input signal, and is operable to divide the input signal into a first part and a second part. In this embodiment, the input signal of the first biorthogonal wavelet filter bank 130 is the raw sound signal x[n], and the first part includes odd components of the input signal and the second part includes even components of the input signal. As shown in FIG. 4, each of the biorthogonal wavelet filter banks 130 includes a first filter set 131 and a second filter set 132. The first filter set 131 has a first high pass filter 131h for filtering the first part of the input signal to output a first high-frequency signal, and a first low pass filter 131g for filtering the first part of the input signal to output a first low-frequency signal.

The second filter set 132 has a second high pass filter 132h for filtering the second part of the input signal to output a second high-frequency signal to be convolved and combined with the first high-frequency signal to form a high-frequency synthesis signal d[n], and a second low pass filter 132g for filtering the second part of the input signal to output a second low-frequency signal to be convolved and combined with the first low-frequency signal to form a low-frequency synthesis signal a[n]. It is worth noting that, the symbol "↓2" represents a downsampling operation for reducing the data rate, and the symbol "$Z^{-1}$" represents a delay function.

Subsequently, one of the high-frequency and low-frequency synthesis signals d[n] and a[n] outputted by a last one of the biorthogonal wavelet filter banks 130 (i.e., the fourth biorthogonal wavelet filter bank 130) serves as the filtered signal, and one of the high-frequency and low-frequency synthesis signals d[n] and a[n] outputted by a previous one of the biorthogonal wavelet filter banks 130 serves as the input signal of a next one of the biorthogonal wavelet filter banks 130 following and adjacent to the previous one of the biorthogonal wavelet filter banks 130.

For example, 16-bit binary coefficients for the respective high pass and low pass filters of the CDF 9/7 tap biorthogonal wavelet filter bank are listed in the following Table 1 and Table 2, respectively. It shouldbe understood that the 16-bit binary coefficients facilitate the hardware implementation.

TABLE 1

| High pass filter | | | |
|---|---|---|---|
| Tap | Second high pass filter | tap | First high pass filter |
| 0'6 | 0000 0101 1101 0111 | 1'5 | 1111 1100 0101 0001 |
| 2'4 | 1101 1010 0010 1001 | 3 | 0100 0111 0010 0011 |

TABLE 2

| Low pass filter | | | |
|---|---|---|---|
| tap | Second low pass filter | tap | First low pass filter |
| 0'8 | 0000 0001 1011 0110 | 1'7 | 1111 1110 1110 1100 |
| 2'6 | 1111 1010 1111 1110 | 3'5 | 0001 0001 0001 0100 |
| 4 | 0010 0110 1001 0111 | | |

In addition, in order to reduce the multiplication steps during the computation, the distributive property is employed. That is, each of the high-frequency and low-frequency synthesis signals d[n] and a[n] can be obtained by distributed arithmetic. In this embodiment, each of the first and second high-frequency signals and the first and second low-frequency signals can be expressed as $$\sum_{n=0}^{N-1} f[n]x[n], \quad (3)$$

$$= \sum_{n=0}^{N-1} f[n] \sum_{i=0}^{M-1} x_i[k]2^i, \quad (4)$$

and $$= \sum_{i=0}^{M-1} 2^i \sum_{n=0}^{N-1} f[n]x_i[n], \quad (5)$$

where $x_i[n]$ represents an $i^{th}$ bit of the raw sound signal x[n], f[n] represents coefficients of a corresponding one of the first and second high pass filters and the first and second low pass filters, N represents a number of the biorthogonal wavelet filter banks 130 of the filtering unit 13, and M represents a number of bits of the raw sound signal x[n] (in this embodiment, M is equal to 8). It is worth mentioning that, all possible values of $$\sum_{n=0}^{N-1} f[n]x_i[n]$$

can be computed in advance and pre-stored in the device 1, and thus can be obtained through table lookup instead of doing multiplications, such that the computation load of the device 1 is further reduced during the operation.

Figure 5:
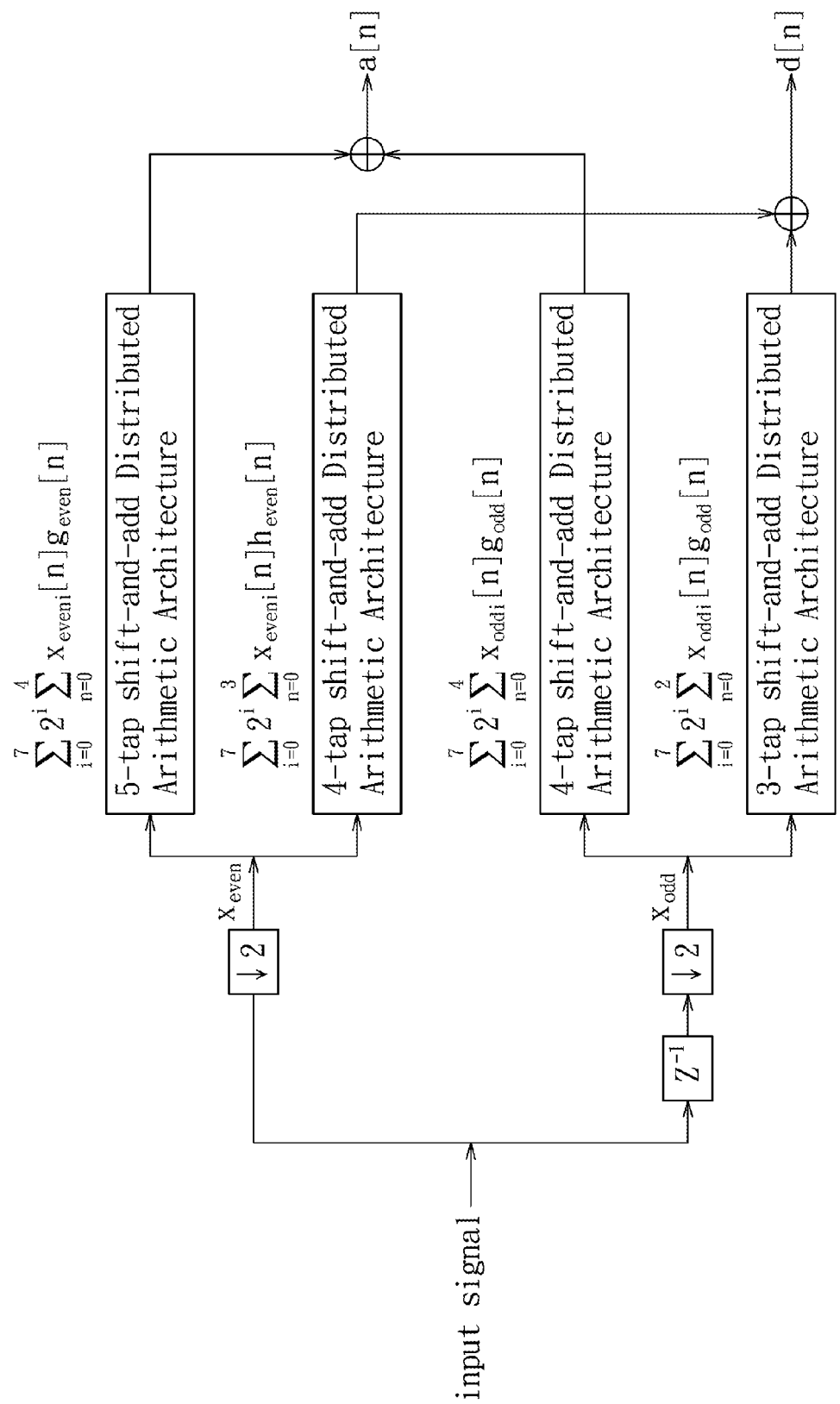
FIG. 5 is a schematic view illustrating the biorthogonal wavelet filter bank using distributed arithmetic to obtain high-frequency and low-frequency synthesis signals.
Figure 7:
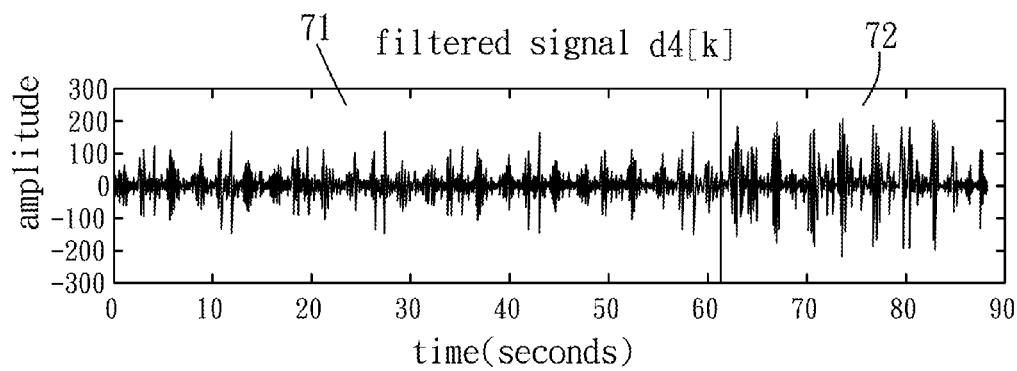
FIGS. 7 and 8 are plots illustrating waveform of a filtered signal obtained from the raw sound signal, and relative energy values associated with the filtered signal, respectively.

FIG. 5 illustrates the polyphase structure of the biorthogonal wavelet filter bank 130 for the above-mentioned distributed arithmetic. The high and low-frequency synthesis signals d[n] and a[n] processed by the biorthogonal wavelet filter bank 130 can be expressed as:

$$d[n] = \sum_{i=0}^{7} 2^i \sum_{n=0}^{3} x_{eveni}[n]h_{even}[n] + \sum_{i=0}^{7} 2^i \sum_{n=0}^{2} x_{oddi}[n]h_{odd}[n], \quad (6)$$

and $$a[n] = \sum_{i=0}^{7} 2^i \sum_{n=0}^{4} x_{eveni}[n]g_{even}[n] + \sum_{i=0}^{7} 2^i \sum_{n=0}^{3} x_{oddi}[n]g_{odd}[n], \quad (7)$$

the filtered signal (d4[k]), which is obtained from the raw sound signal x[n] using the biorthogonal wavelet filter bank 130 illustrated in FIG. 6, is shown in FIG. 7. Specifically, the filtered signal includes a first filtered portion 71 and a second filtered portion 72 that correspond respectively to the first portion 61 and the second portion 62 in the time domain. It can be noted, from FIGS. 6 and 7, that the second filtered portion 72 has relatively larger amplitude.

After the filtered signal is obtained, in step S3, the identifying unit 14 is operable to compute an energy value of each of the sections of the filtered signal, and then, to compute a relative energy value by dividing the energy value by a given average energy value. Specifically, the energy value and the corresponding relative energy can be computed based upon:

$$E_j = \sum_{k=m_j}^{m_j+F-1} d_j[k]^2, \quad (8)$$

and $$RWE = \frac{E_j}{E_{normal}}, \quad (9)$$

where $E_j$ represents the energy value of a corresponding one of the sections of the filtered signal within the specific frequency bandwidth j, k represents the sample points in the corresponding one of the sections, $E_{normal}$ represents the given average energy value, F represents a number of the sample points in the corresponding one of the sections (e.g., 512 in this embodiment), and RWE represents the relative energy value. It should be noted that the given average energy value ($E_{normal}$) is computed using Equation (8), in advance, as an average value of energy values of respective sections of a filtered signal from a normal lung sound (i.e., without wheeze).

Afterward, in step S4, the identifying unit 14 is operable to determine whether the relative energy values (RWE) of apart of the sections are larger than a threshold value, and duration of said part of the sections is longer than a predetermined observation time in the time domain. When the relative energy values (RWE) are greater than the threshold value and the duration of said part of the sections is longer than the predetermined observation time, the flow goes to step S5. Otherwise, the flow goes to step S7. In this embodiment, the predetermined observation time is 0.25 second, and the threshold value is 4. However, the threshold value may vary among different users and occasions, and is not limited to the disclosure.

In step S5, the identifying unit 14 is operable to determine that a wheeze occurs in the lung sound, and to generate and send an alert signal to the alert unit 15. Then, in step S6, the alert unit 15 is operable, upon receipt of the alert signal, to generate an alert output to warn that a wheeze occurs in the lung sound. On the other hand, in step S7, the identifying unit 14 is operable to determine that the lung sound is normal. Specifically, the alert output includes at least one of an audio output and a visual output. That is, when the lung sound of the patient has wheeze, the device 1 is capable of immediately producing an alert. In this embodiment, the alert unit 15 includes a speaker for generating the audio output, and/or a light emitting diode (LED) for generating the visual output.

Figure 8:
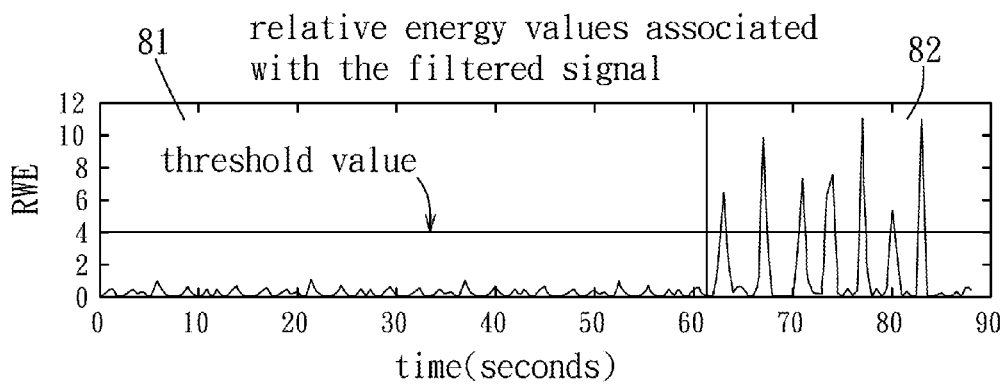

For example, the relative energy values RWE corresponding to the filtered signal are shown in FIG. 8 with the threshold value equal to 4. Similar to FIGS. 6 and 7, the relative energy values include a first RWE portion 81 corresponding to the first filtered portion 71 in FIG. 7, and a second RWE portion 82 corresponding to the second filtered portion 72 in FIG. 7. It can be seen that, in the second RWE portion 82, the RWE of some of the sections are larger than 4, and the durations of these sections are clearly longer than 0.25 second. In such case, the identifying unit 14 is operable to determine that a wheeze occurs in the lung sound.

It should be noted that, in other embodiments, it may be not necessary to compute the relative energy (RWE), and therefore, a predetermined value (i.e., a product of the given average energy value ($E_{normal}$) and the threshold value) is pre-computed and pre-stored in the device 1. Thus, the identifying unit 14 can be configured, in steps S4 and S5, to determine that a wheeze occurs in the lung sound when the energy values ($E_j$) of a part of the sections are larger than the predetermined value and duration of said part of the sections is longer than the predetermined observation time (e.g., 0.25 second) in the time domain.

To sum up, by virtue of the configuration of the biorthogonal wavelet filter banks 130 with the polyphase structure, the device 1 is able to process the lung sound to obtain the filtered signal with relatively greater accuracy. Further, the device 1 is able to monitor the lung sound of a patient in the real-time.

While the present invention has been described in connection with what is considered the most practical and preferred embodiment, it is understood that this invention is not limited to the disclosed embodiment but is intended to cover various arrangements included within the spirit and scope of the broadest interpretation so as to encompass all such modifications and equivalent arrangements.

What is claimed is:

1. A device for detecting occurrence of wheeze in a lung sound, said device comprising:
   an acoustic processing unit for obtaining a lung sound and for generating a raw sound signal in time domain accordingly;
   a filtering unit for filtering the raw sound signal to obtain a filtered signal within a specific frequency bandwidth, the filtered signal having a plurality of sections with respect to the time domain; and
   an identifying unit for computing an energy value of each of the plurality of the sections of the filtered signal, and for determining that a wheeze occurs in the lung sound when energy values of a part of the plurality of the sections are larger than a predetermined value and duration of said part of the sections is longer than a predetermined observation time in time domain;
   wherein said filtering unit includes a plurality of biorthogonal wavelet filter banks connected in series, and each of the plurality of said biorthogonal wavelet filter banks of said filtering unit has a polyphase structure;

wherein, in the polyphase structure, each of the plurality of said biorthogonal wavelet filter banks receives an input signal, divides the input signal into a first part and a second part, and includes a first filter set having a first high pass filter for filtering the first part of the input signal to output a first high-frequency signal, and a first low pass filter for filtering the first part of the input signal to output a first low-frequency signal, and a second filter set having a second high pass filter for filtering the second part of the input signal to output a second high-frequency signal, the second high-frequency signal being combined with the first high-frequency signal to form a high-frequency synthesis signal, and a second low pass filter for filtering the second part of the input signal to output a second low-frequency signal, the second low-frequency signal being combined with the first low-frequency signal to form a low-frequency synthesis signal;

wherein, the raw sound signal from said acoustic processing unit serves as the input signal of a first one of the plurality of said biorthogonal wavelet filter banks of said filtering unit, one of the high-frequency and the low-frequency synthesis signals outputted by a last one of the plurality of said biorthogonal wavelet filter banks serves as the filtered signal, and one of the high-frequency and the low-frequency synthesis signals outputted by one of the plurality of said biorthogonal wavelet filter banks serves as the input signal of a next one of the plurality of said biorthogonal wavelet filter banks immediately following said one of the plurality of said biorthogonal wavelet filter banks.

2. The device as claimed in claim 1, wherein each of the plurality of said biorthogonal wavelet filter banks is a Cohen-Daubechies-Feauveru (CDF) 9/7 tap biorthogonal wavelet filter bank.

3. The device as claimed in claim 1, wherein each of the high-frequency and the low-frequency synthesis signals is obtained by distributed arithmetic, in which each of the first and the second high-frequency signals and the first and second low-frequency signals satisfies $$\sum_{i=0}^{M-1} 2^i \sum_{n=0}^{N-1} f[n]x_i[n],$$

where $x_i[n]$ represents an $i^{th}$ bit of the raw sound signal $x[n]$, $f[n]$ represents coefficients of a corresponding one of said first and second high pass filters and said first and second low pass filters, N represents the number of said biorthogonal wavelet filter banks of said filtering unit, and M represents a number of bits of the raw sound signal.

4. The device as claimed in claim 1, wherein the specific frequency bandwidth of the filtered signal obtained by said filtering unit ranges from 250 Hertz to 500 Hertz.

5. The device as claimed in claim 1, wherein said identifying unit is operable to further compute relative energy values respectively by dividing the energy values of the plurality of the sections of the filtered signal by a given average energy value, and to determine that a wheeze occurs in the lung sound when the relative energy values associated with the energy values of the part of the plurality of the sections are larger than a threshold value and duration of the part of the plurality of the sections is longer than the predetermined observation time in the time domain.

6. The device as claimed in claim 1, further comprising an alert unit, wherein:

said identifying unit is operable to further generate an alert signal to said alert unit upon determination of the occurrence of the wheeze in the lung sound; and said alert unit is operable, upon receipt of the alert signal, to generate an alert output to warn that a wheeze occurs in the lung sound.

7. The device as claimed in claim 6, wherein the alert output includes at least one of an audio output and a visual output.

8. The device as claimed in claim 1, wherein the predetermined observation time is 0.25 second.

9. The device as claimed in claim 1, further comprising a body at which said acoustic processing unit, said filtering unit and said identifying unit are disposed.

10. A method for detecting an occurrence of a wheeze in a lung sound, said method to be implemented by a detecting device, said method comprising the following steps of:

A) configuring the detecting device to obtain a lung sound and to generate a raw sound signal in time domain accordingly;

B) configuring the detecting device to filter the raw sound signal to obtain a filtered signal within a specific frequency bandwidth, the filtered signals having a plurality of sections with respect to the time domain;

C) configuring the detecting device to compute an energy value of each of the plurality of the sections of the filtered signal; and D) configuring the detecting device to determine that the wheeze occurs in the lung sound when energy values of a part of the plurality of the sections are larger than a predetermined value and duration of said part of the sections is longer than a predetermined observation time in the time domain;

wherein the detecting device includes a plurality of biorthogonal wavelet filter banks connected in series, and each of the plurality of the biorthogonal wavelet filter banks has a polyphase structure;

wherein, in the polyphase structure, each of the plurality of said biorthogonal wavelet filter banks receives an input signal, divides the input signal into a first part and a second part, and includes a first filter set having a first high pass filter for filtering the first part of the input signal to output a first high-frequency signal, and a first low pass filter for filtering the first part of the input signal to output a first low-frequency signal, and a second filter set having a second high pass filter for filtering the second part of the input signal to output a second high-frequency signal, the second high-frequency signal being combined with the first high-frequency signal to form a high-frequency synthesis signal, and a second low pass filter for filtering the second part of the input signal to output a second low-frequency signal, the second low-frequency signal being combined with the first low-frequency signal to form a low-frequency synthesis signal;

wherein, the raw sound signal from said acoustic processing unit serves as the input signal of a first one of the plurality of said biorthogonal wavelet filter banks of said filtering unit, one of the high-frequency and the low-frequency synthesis signals outputted by a last one of the plurality of said biorthogonal wavelet filter banks serves as the filtered signal, and one of the high-frequency and the low-frequency synthesis signals outputted by one of the plurality of said biorthogonal wavelet filter banks serves as the input signal of a next one of the plurality of said biorthogonal wavelet filter banks immediately following said one of the plurality of said biorthogonal wavelet filter banks.

11. The method as claimed in claim 10, wherein, in step B), the specific frequency bandwidth ranges from 250 Hertz to 500 Hertz.

12. The method as claimed in claim 10, wherein, in step C), the detecting device is configured to further compute relative energy values respectively by dividing the energy values of the plurality of the sections of the filtered signal by a given average energy value, and to determine that a wheeze occurs in the lung sound when the relative energy values associated with the energy values of the part of the plurality of the sections are larger than a threshold value and a duration of the part of the plurality of the sections is longer than the predetermined observation time in the time domain.

13. The method as claimed in claim 10, further comprising, after step D), the following step of:
    configuring the detecting device to generate an alert output to warn that the wheeze occurs in the lung sound.

14. The method as claimed in claim 13, wherein the alert output includes at least one of an audio output and a visual output.

15. The method as claimed in claim 10, wherein the predetermined observation time is 0.25 second.

\* \* \* \* \*